United States Patent [19]
Rothschild et al.

[11] Patent Number: 5,930,326
[45] Date of Patent: Jul. 27, 1999

[54] SIDE SCATTER TOMOGRAPHY SYSTEM

[75] Inventors: Peter Rothschild, Chestnut Hill; Lee Grodzins, Lexington, both of Mass.

[73] Assignee: American Science and Engineering, Inc., Billerica, Mass.

[21] Appl. No.: 08/890,957

[22] Filed: Jul. 8, 1997

Related U.S. Application Data

[60] Provisional application No. 60/021,267, Jul. 17, 1996.
[51] Int. Cl.$^6$ .................................................. G01N 23/04
[52] U.S. Cl. .................................. 378/57; 378/86; 378/87
[58] Field of Search .................................. 378/57, 51, 86, 378/87, 88, 89, 90, 62, 6

[56] References Cited

U.S. PATENT DOCUMENTS 5,642,394  6/1997  Rothschild .................................. 378/57
5,696,806  12/1997  Grodzins et al. .......................... 378/86

*Primary Examiner*—David P. Porta
*Attorney, Agent, or Firm*—Bromberg & Sunstein LLP

[57] ABSTRACT

An x-ray tomography system measures x-rays side-scattered by material concealed within an enveloping surface. One or more x-ray beams are incident on the enveloping surface and scattered onto collimated detectors disposed in arrays parallel to the incident x-ray beams. By varying the relative orientation of the enveloping surface with respect to the x-ray beams and measuring the x-rays side-scattered by the material concealed within the enveloping surface, the shape, density, position and composition of the contents of the enveloping surface may be mapped.

33 Claims, 6 Drawing Sheets

SIDE SCATTER TOMOGRAPHY SYSTEM

The present application claims priority from U.S. provisional application Ser. No. 60/021,267, filed Jul. 17, 1996, which is herein incorporated by reference.

FIELD OF THE INVENTION

The present invention relates to a system and method for determining the shape, position, density, and composition of objects that have been concealed in an enveloping surface such as a piece of airline baggage or a shipping container. It is suited to detecting concealed contraband, such as explosives (and, in particular, sheet explosive and plastic explosive hidden in an electronic device), weapons or drugs.

BACKGROUND OF THE INVENTION

Various methods for using penetrating radiation such as x-rays in order to probe the contents of a sealed container such as airline baggage have been developed over the years. Some of these use the signature of x-rays scattered in various directions by material within the container. Since the cross-section for scattering is generally small, which is to say that only a small fraction of the incident beam is scattered into the acceptance solid angle of any particular detector, efficient strategies are necessary in order to discriminate threat items from the general background.

Furthermore, the detection of sheet explosive, concealed in the lining of suitcases or other containers, remains a particularly difficult challenge for traditional x-ray detection systems. This is because sheet explosives may be very thin, possibly no thicker than 2 mm. X-ray backscatter systems provide a means of detecting sheet explosives, but can generally only find a sheet when it is on the side of the container close to the backscatter detectors. Sheet explosives concealed in the lining on the other sides of the container will often not be found.

A further challenge to explosives detection is the concealment of explosives in electronic devices such as personal computers, radios, and cassette recorders, all of which make excellent hiding places for concealing explosives because an electronic device is not easily opened by security personnel for inspection and because electronic devices appear very cluttered in x-ray transmission images, making it easy to conceal an explosive with its associated detonator, trigger system, batteries, and wires within the electronic device.

SUMMARY OF THE INVENTION

In accordance with one aspect of the invention, in one of its embodiments, there is provided a side scatter tomography system for analyzing material such as an object concealed within an enveloping surface. The side scatter tomography system has one or more sources of penetrating radiation emitting a beam along a beam axis disposed with an orientation with respect to the enveloping surface. The system also has one or more arrays of segmented detectors disposed along a detector axis substantially parallel to the beam axis for detecting scattered radiation and producing signals corresponding at least to the scattered radiation. Additionally, the tomography system has a scanner arrangement for varying the orientation of the beam axis with respect to the material. The tomography system may also have a controller for processing the signals produced by the segmented detectors.

In accordance with alternate embodiments of the invention, the tomography system may also have at least one transmission detector disposed along the beam axis for measuring penetrating radiation transmitted through the material and a conveyor for transporting the material. The scanner arrangement may include a scanner for raster-scanning the beam axis in a plane transverse to the beam axis. In accordance with an alternate embodiment of the invention, the source or sources of penetrating radiation emit radiation at energies less than 450 keV. The tomography system may have both a first beam of penetrating radiation and a second beam of penetrating radiation counterpropagating to the first beam, and the counterpropagating beams may be alternatingly illuminated. The tomography system may also have a plurality of collimators disposed in directions perpendicular to the beam axis for limiting the field of view of each segmented detector.

In accordance with a further aspect of the present invention, there is provided a method for analyzing material having edges, where the material is concealed within an enveloping surface. The method has the steps of illuminating the enveloping surface with penetrating radiation propagating substantially along a beam axis, measuring a profile of penetrating radiation side-scattered by the concealed material, and locating the edges of the material on the basis of a profile of penetrating radiation side-scattered by the concealed material. In accordance with alternate embodiments of the invention, the step of locating the edges of the material may include detecting discontinuities in the profile of side-scattered penetrating radiation. The method may also include the step of determining the dimensions of the concealed material along the beam axis.

In accordance with other alternate embodiments of the invention, the method may also include measuring penetrating radiation transmitted through the material, calculating an attenuation of penetrating radiation attributable to the material, deriving an attenuation per unit length characteristic of the material, and calculating the density of the concealed material on the basis of the attenuation and dimensions of the material.

In accordance with other alternate embodiments of the invention, the method may also include raster-scanning the beam axis in a plane transverse to the beam axis, determining the three-dimensional shape of the concealed material on the basis of edges with respect to a plurality of beam positions, and imaging the concealed material. The method may include the further steps of comparing the attenuation of penetrating radiation per unit length in the concealed material with tabulated values and determining the composition of the concealed material. The method may also include comparing the density of the concealed material with tabulated values and determining the composition of the concealed material.

In accordance with yet further alternate embodiments of the invention, the method may include the steps of locating the material in the attenuation-thickness plane for determining a composition of the concealed material as well as the step of categorizing a degree of threat constituted by said material. The method may also include the step of conveying the enveloping surface in a direction perpendicular to the beam axis. Edges of the concealed material may be located by detecting a peak in the side-scattered radiation. The step of illuminating the enveloping surface with penetrating radiation may include alternating between illumination by two counterpropagating beams.

The method for analyzing a material may also include deriving an attenuation of scattered radiation in a direction transverse to the beam axis, deriving an atomic number of the concealed material on the basis of at least the ratio of the attenuation of the illuminating penetrating radiation to the attenuation of the scattered radiation, correcting a calculated scatter per unit volume for matter intervening between the concealed material and the detector array, identifying types of objects concealed within the enveloping surface on the basis of the spread in measured attenuation over a specified volume of the enveloping surface, and comparing calculated scatter per unit volume against an expected scatter per unit volume based on the identified type of object concealed within the enveloping surface. The surface may be illuminated alternatingly with differing energy distributions in order to determine an effective atomic number corresponding to the concealed material on the basis of the ratio of penetrating radiation transmitted through the material at a first and a second energy distribution.

DETAILED DESCRIPTION OF PREFERRED EMBODIMENTS

Figure 1:
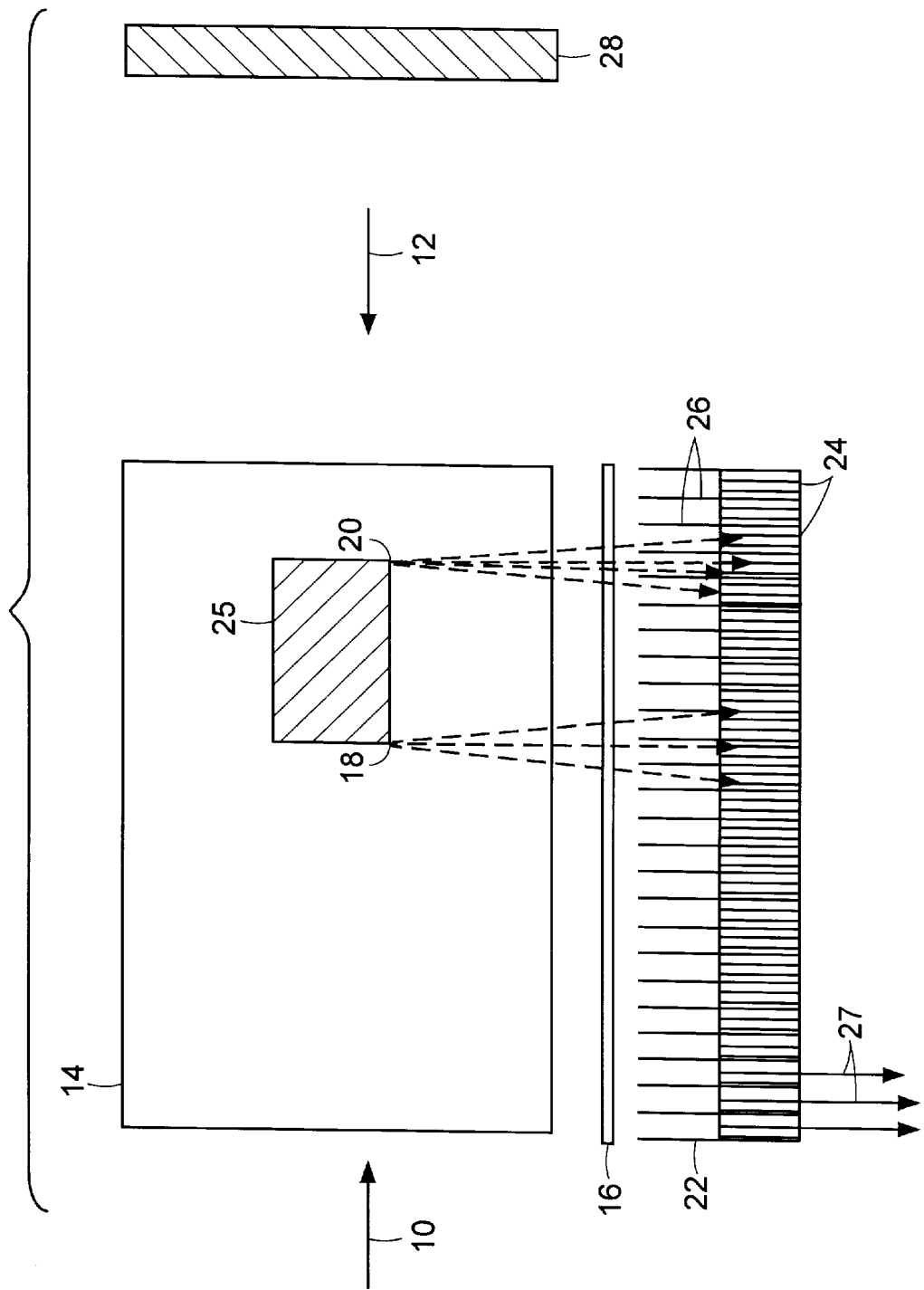
FIG. 1 is a schematic representation of a two-beam x-ray tomography system in accordance with one embodiment of the invention.

The detection and identification of objects concealed within a container by use of side-scattered penetrating radiation is amenable to many embodiments which may be practiced within the scope of the appended claims. A first embodiment is described with reference to FIG. 1, wherein a left beam 10 of penetrating radiation and a right beam 12 of penetrating radiation are incident on opposite sides of an enveloping surface such as a container 14. Beams 10 and 12 of penetrating radiation, may be, for example, beams of x-rays such as polychromatic x-ray beams having the same or different distributions of energy. Beams 10 and 12 will be referred to in the present description, without limitation, as x-ray beams. Container 14 may be any sort of enveloping surface which prevents the nature of its contents from being readily apparent and may include, for example, a suitcase or other sort of cargo, a car, truck, or other vehicle, an article of clothing, or a person or other subject. The orientation of container 14 is varied with respect to beams 10 and 12 so that beams 10 and 12 are incident upon container 14 at a variety of positions in temporal sequence. In the preferred embodiment, container 14 moves horizontally past beams 10 and 12 on a conveyor belt 16 as beams 10 and 12 are raster-scanned in the vertical direction. In an alternative embodiment, beams 10 and 12 may be scanned in the horizontal direction as well, since horizontal motion of the beam serves the same function of scanning the beams relative to container 14 as does the motion of container 14 on conveyor belt 16. Left and right polychromatic x-ray beams 10 and 12 have a maximum energy typically between 200 and 450 KeV, in order to provide a flux on the order of $2 \times 10^9$ photons per second in each beam, though other energy ranges and fluxes may be used. In the preferred embodiment, the two beams 10 and 12 pass through approximately the same path through the container 14 at the same time, but in opposite directions. At each point in time this path is known. In an alternative embodiment, the two beams 10 and 12 can be made to alternate in time, so that the scattered x-rays 18 from the left beam 10 can be clearly distinguished from the scattered x-rays 20 from the right beam 12.

Two arrays 22 of segmented detectors (or "counters") 24 are positioned so as to detect scattered x-rays 18 and 20 scattered by a concealed object 25 at angles of approximately 90 degrees from the propagation directions of the beams. Note that only the lower array 22 below conveyor 16 is shown in FIG. 1. The detectors 24 employ x-ray detection techniques known to persons skilled in the art. By way of example, detectors 24 may be BGO crystals with photodiodes or, alternatively, CsI crystals and photomultiplier tubes may be used. In the preferred embodiment, fiber optic links 27 couple detectors 24 to photomultipliers (not shown). Another detector array 22 may be located above container 14 as it is carried along conveyor 16. The scatter detector arrays 22 are segmented along the direction of the incident beams 10 and 12 into individual detector elements 24. The detector elements 24 may be long relative to the smallest dimensions of the cross-sections of beams 10 and 12 and are typically 15–30 cm in the direction of conveyor 16, which is the direction into the page of FIG. 1. The length of detector elements 24 serves to increase the solid angle subtended by the element. Detector arrays 22 are collimated by collimator sheets 26 so that each detector element 24 detects x-rays 18 and 20 scattered from a different slice of container 14. In this way, the intensity of the side-scattered radiation 18 and 20 can be mapped as a function of distance along the beam through container 14. The resolution of the mapping is determined by the width of the detector elements 24 and the thickness of the collimator sheets 26. A width of 0.5 cm for the detector elements 24 with 1 mm thick sheets of tungsten for the collimators 26 provides a good compromise between resolution and photon statistics.

In addition to scatter detector arrays 22, a transmission detector 28 measures the flux from left x-ray beam 10 that penetrates container 14. In an airport baggage surveillance environment, typically 20–30% of the incident flux from left x-ray beam 10 is transmitted through container 14.

Figure 2:
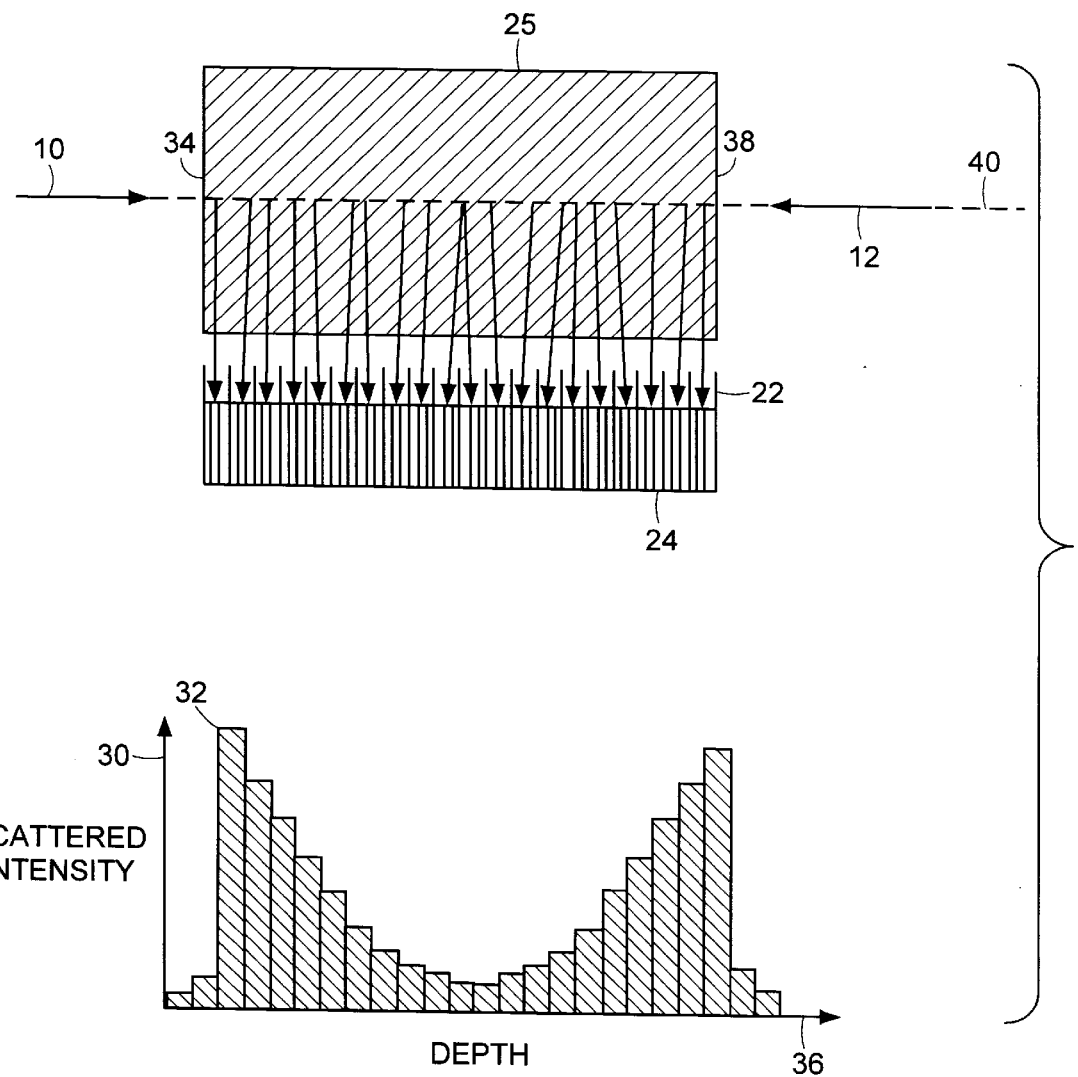
FIG. 2 provides a plot showing the distribution of side-scattered intensity of an object as viewed using the embodiment of the invention of FIG. 1.

Operation of the transmission aspect of the invention is described with reference to FIG. 2. The invention uses a mapping of the intensity of side-scattered x-rays as a function of depth into the container to determine the dimensions of concealed object 25. In particular, the edges of low-Z objects (such as plastics or explosives) that are nearest the beam entry point exhibit enhanced Compton scattering in the direction perpendicular to the incident beam. The side-scatter intensity distribution, plotted along vertical axis 30, exhibits a peak 32 at the object edge 34, with a fall-off in the intensity as the distance into the object, plotted along horizontal axis 36, increases. By using two beams 10 and 12 incident on object 25 from opposite sides, both edges 34 and 38 of object 25 along the line-of-sight 40 of beams 10 and 12 can be detected and the dimension of object 25 along beam direction 40 can easily be obtained.

Once the dimension of concealed object 25 along the line-of-sight 40 of the beam has been determined, the attenuation of the beam in the object can be used to determine the density of the object. The transmitted flux when the beam is passing through the object is given by $$I_t = I_o \exp(-\mu t) \quad (1)$$

where $I_0$ is the transmitted intensity when the beam is dose to the object but not passing through it, $\mu$ is the linear attenuation coefficient for x-rays in the object material and t is the dimension of the object along the line of sight of the beam. By measuring the ratio $I_t/I_o$ and using t measured from the side-scatter intensity distribution, $\mu$ for the material can be determined. Note that $\mu$ is the attenuation per unit length of material. This is the important point that distinguishes the invention from other approaches. For example, explosives and plastics have a similar attenuation for x-rays per unit mass of material. However, because the density of explosives is typically 20–60% higher than for plastics, the attenuation per unit length of material can be significantly different. The invention exploits this difference to distinguish explosives from other low-Z materials such as plastics.

For low-Z materials, at x-ray energies above 50 keV, the interaction of x-rays in the material is almost solely due to Compton scattering. The linear attenuation coefficient is therefore proportional to the electron density of the material, which, in turn, is proportional to the material density. Therefore, measuring $\mu$ yields the density of the material.

The algorithm that reconstructs objects inside the container is very simple compared with the more complicated algorithms used in CT systems. The first step is to identify peaks in the side scatter intensity distribution with edges of objects. Peaks which appear in the distributions of both beams (for the same beam path through the container) are due to opposite edges of the same object. This allows the peaks to be paired with one another, and the thickness t of the object along the beam path is simply the distance between the paired peaks. Note that in addition to measuring the thickness of the object along the beam path, this technique allows for a complete mapping of the object surface in 3-dimensional space as the beams raster-scan the entire object. Furthermore, the mapping may be stored internally, or displayed visually, with a location in a memory array or on a display device corresponding to a position within the scanned container, thereby imaging the container and the objects concealed therein.

The second step of the algorithm is to determine $\mu$ the linear attenuation coefficient of the objects in the container. Once the edges of an object in the plane perpendicular to the x-ray beams have been found, the ratio $I_t/I_o$ can be measured at several locations around the edges. $I_t$ is the transmitted intensity just inside the object at one such location (called point a) on an edge of the object, and $I_0$ is the transmitted intensity at a position (called point b) just outside the object, but in close proximity to point a. The thickness t of the object along the beam at point a has been determined from the side scatter distribution. Equation 1 then yields the value of $\mu$ for the object. A lookup table can then be used to identify the material making up the object.

Figure 3:
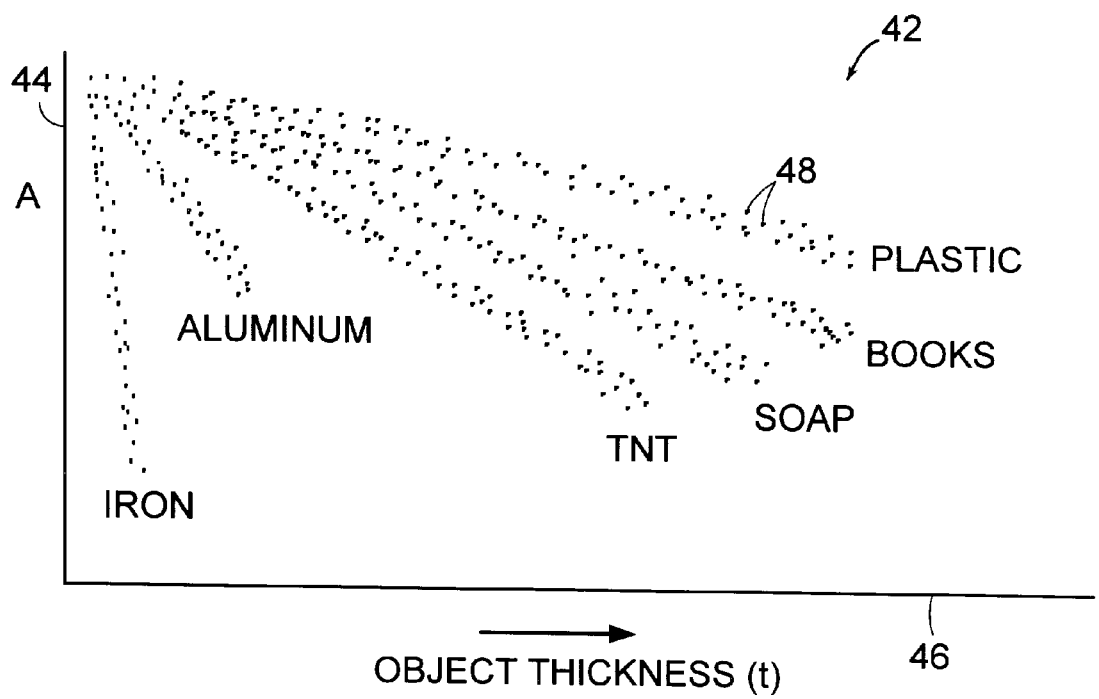
FIG. 3 provides a plot showing the attenuation-vs.-thickness points characteristic of different materials making up a concealed object as viewed using the invention.

An alternative derivation of the composition of a concealed object is described with reference to FIG. 3. The scatter plot 42 shows attenuation of x-rays within the object, as described by $$A = -\mu t = \log(I_t/I_o), \quad (2)$$

and plotted, along vertical axis 44, against the object thickness t (plotted along horizontal axis 46), which has been determined as described above. The position of the points 48 in the (t,A) plane depends on the material making up the object. A region of the plane containing most of the points corresponding to explosives (for example) can be defined as a threat region, and objects lying in this region are identified as explosives.

Figure 4:
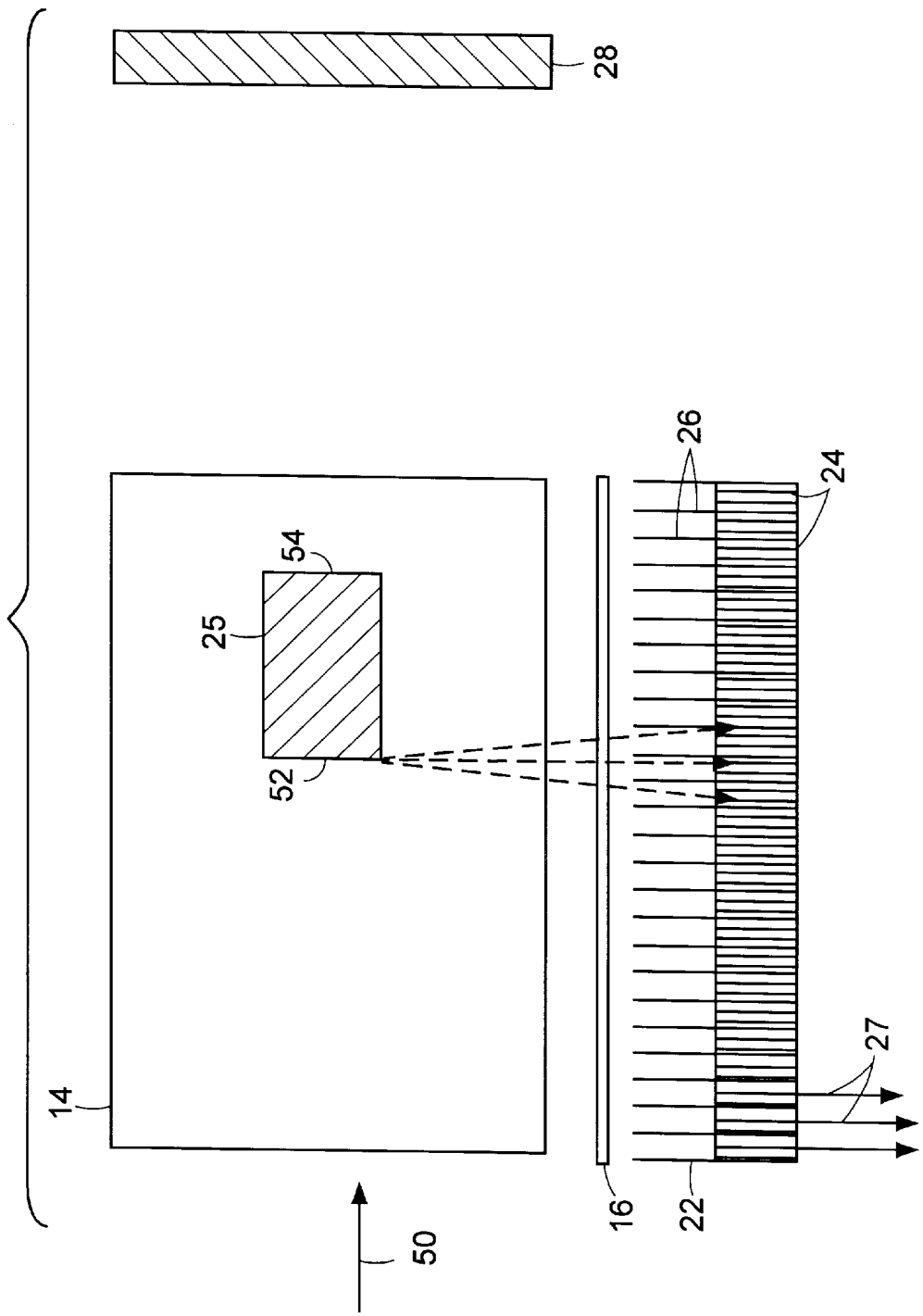
FIG. 4 is a schematic representation of a single-beam embodiment of the invention.
Figure 5:
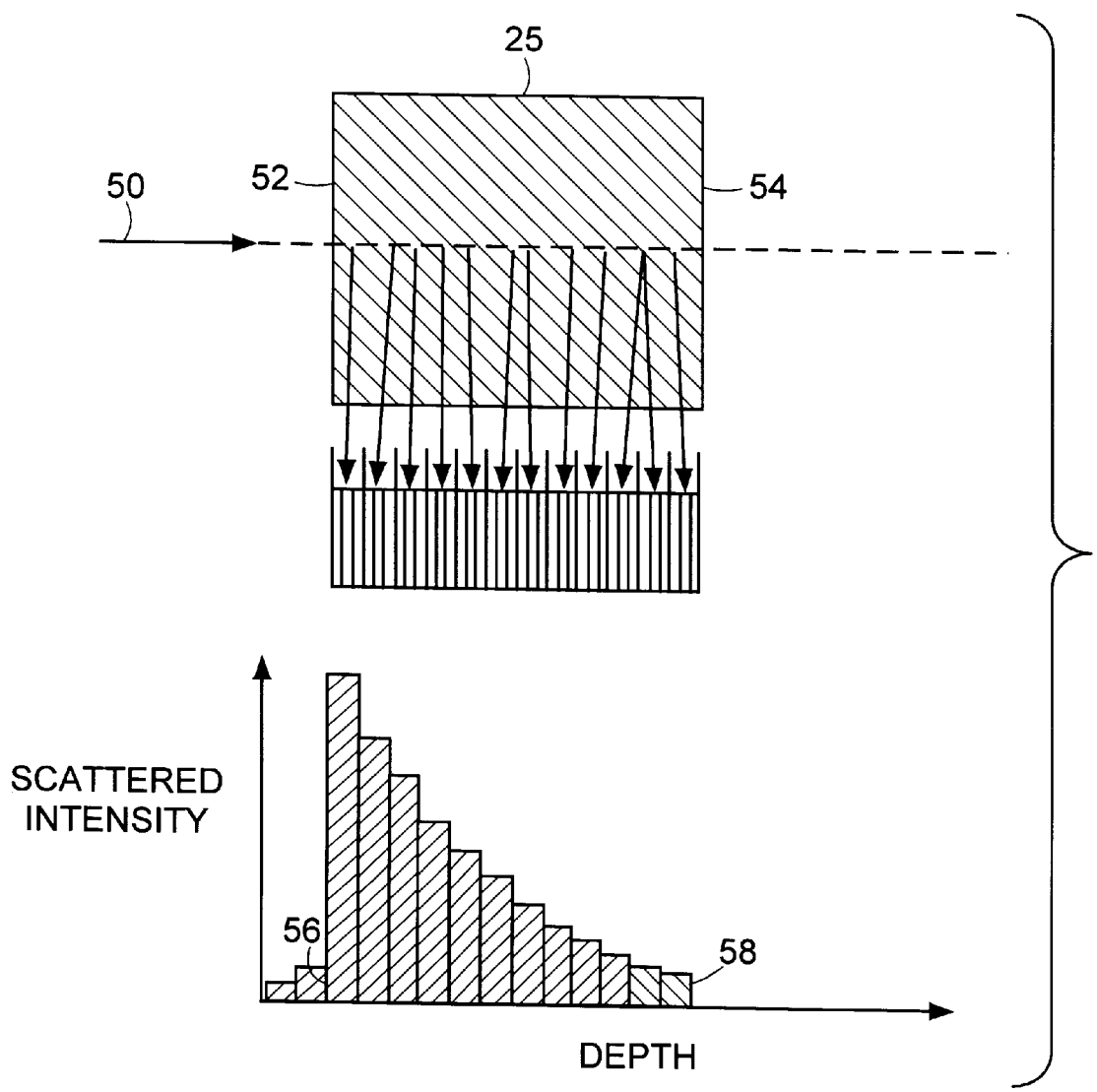
FIG. 5 provides a plot showing the intensity distribution of x-rays side-scattered from an object as viewed using the single-beam embodiment of FIG. 4.

A second embodiment of the invention, effective for inspecting smaller containers or containers with less absorption, is described with reference to FIGS. 4 and 5. A single x-ray beam 50 is used to measure the dimension of concealed object 25 along the beam. In this case, both the entry point 52 and exit point 54 of incident beam 50 with the object 25 can be determined from the detected x-ray intensities I in the segmented side-scatter detectors 24. In this embodiment, the left edge 52 gives rise to a marked increase 56 in scattering intensity I, while an abrupt fall-off 58 in the increased scattering intensity I occurs at right edge 54 of concealed object 25. The left and right edges 52 and 54 are thus automatically paired, making the analysis somewhat easier. In addition, the cost is lowered by requiring only one x-ray source and for small containers where the absorption is low, only one scatter detector array 22 is required.

Figure 6:
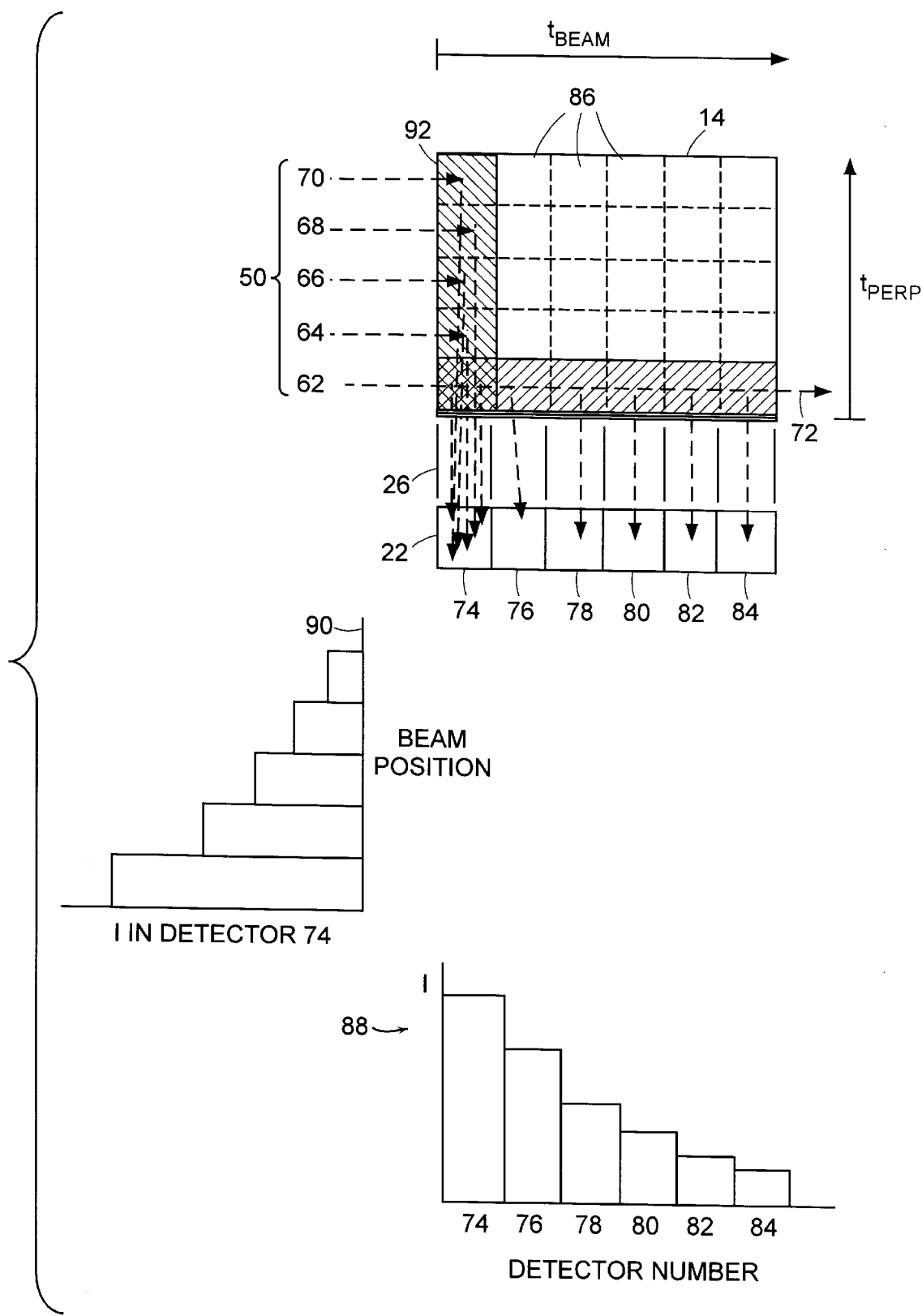
FIG. 6 provides a plot illustrating the use of side-scatter beam attenuation to derive the density of a concealed object using the single-beam embodiment of FIG. 4.

A third embodiment of the invention is described with reference to FIG. 6. Container 14 is moved relative to x-ray beam 62 in a direction corresponding to the direction out of the plane of the paper. Container 14 is moved in this direction by a conveyor (not shown) or by other equivalent means. For example, the x-ray source may, equivalently, be translated in the same direction, into the plane of the paper. X-ray beam 62 is shown as successive beams 62, 64, 66, 68, and 70. All of successive x-ray beams 62, 64, 66, 68, and 70 penetrate container 14, with the continuation of beam 62 to exit as beam 72 shown by way of example. X-rays scattered approximately perpendicularly to successive beams 62, 64, 66, 68, and 70 are detected in side scatter detector array 22 of detectors (or counters). Representative counters 74, 76, 78, 80, 82, and 84 are shown below container 14. The field of view of each of detectors 74, 76, 78, 80, 82, and 84 is collimated by fins 26 so as to count scattered x-rays from a narrow range of positions along each of successive beam directions 62, 64, 66, 68, and 70. The overall width of detector array 22 substantially covers the width of the conveyor.

When x-ray beam 50 is in its lower position 62, for example, beam 62 penetrates through the lowest set of the pixels (designated collectively by numeral 86) into which the cross section of container 14 is conceptually divided. The intensities I of x-rays scattered downward into detectors 74–84 are represented schematically by histogram 88. Each of detectors 74–84 measures x-rays from successive, known lengths of the contents of container 14. The histogram of counts in detectors 74–84 represents the characteristic attenuation curve for the object within container 14 for the energy spectrum of x-rays penetrating container 14. The histogram is described by the attenuation equation:

$$I = I_0(E_{inc})e^{-\mu t_{beam}}, \quad (3)$$

where $I_0$ is the intensity of the incident beam, $\mu$ is the linear attenuation coefficient of the material within container 14, and t is the distance in the object along the beam direction that is viewed at a given moment by each of the detectors 74–84.

Casting eq. 3 in logarithmic form, $$\log\left[\frac{I_0(E_{inc})}{I}\right] = \mu t_{beam}, \quad (4)$$

the linear attenuation coefficient is given by the slope of the curve of relative intensity versus distance, i.e., detector position. Thus, the measure of the ratios of intensities of x-rays scattered from elements in the object along the beam path through the object gives a direct measure of $\mu$ which is independent of geometrical effects, such as the position of the object with respect to the incident beam of the detectors.

The linear attenuation coefficients are given explicitly by the equation:

$$\mu = \sigma_{total}\left(\frac{N_0}{A}\right)\rho, \quad (5)$$

where $N_0$ is Avogadro's number, A is the atomic weight of the object and $\rho$ is its density. The total cross section for the x-ray interactions, $\sigma_{total}$, is mainly due to the Compton effect for a wide range of x-ray energies. Thus, eq.. 3 can be well approximated by:

$$\mu = \sigma_{electron}\left(\frac{Z}{A}\right)N_0\rho. \quad (6)$$

The Compton scattering cross section per electron is a constant, and Z/A varies by only about ±10% over most of the periodic table. Thus a measure of $\mu$ gives a direct measure of the density of an object concealed within container 14.

As beam 50 sweeps upward, moving, successively, through positions 62–70, the intensity I of the scattered x-rays detected in detector 74 decreases, reflecting the fact that the scattered beam is itself attenuated as it passes through an increasing number of pixels 86 of container 14 between the scattering object and detector 74. A representative histogram 90 of the intensity I of scattered x-rays is shown. The equation describing histogram 90 is similar in form to eqn. 3, with the linear attenuation coefficient p relating to the energies of the scattered rather than the incident x-rays:

$$I = I_0(E_{scatter})e^{-\mu t_{prep}}, \quad (7)$$

or, in logarithmic form, $$\log\left[\frac{I_0(E_{scatter})}{I}\right] = \mu t_{perp}. \quad (8)$$

Again, the linear attenuation $\mu$ is given by the slope of the relative intensities versus distance so that the measurements are independent of geometrical considerations.

The scattered x-rays are typically lower in energy than the incident x-rays. Thus, as the x-ray beam scans the volume of container 14 near its front face 92, two measures of its density are obtained.

By combining eqs. 4 and 8, a mean atomic number corresponding to the scattering object may be obtained. Dividing one equation by the other, an equation is obtained which depends only on known distances and the ratio of the mean cross sections at the incident and scattered energies:

$$\frac{\log\left[\frac{I_0(E_{inc})}{I}\right]}{\log\left[\frac{I_0(E_{scatter})}{I}\right]} = \frac{\sigma(E_{inc})t_{beam}}{\sigma(E_{scatter})t_{perp}}. \quad (9)$$

The ratio of the cross sections at two different energies, one of which is more sensitive to the photoelectric effect than the other, is well-known to be a sensitive measure of atomic number. By adjusting the incident energy for a specified application, both the mean density and the mean atomic number of an object may be determined in one x-ray sweep of the face of container 14.

As container 14 moves through the restart beam 50, histograms similar to 88 and 90 are obtained. Thus, the mean density and atomic number of an object are obtained from a large number of independent measurements if, as is generally the case, the object is large compared to the dimensions of the x-ray beam and the spatial resolution of the detectors.

The side scatter tomography system described with reference to FIGS. 1–6, additionally provides a useful means for measuring the x-rays scattered from all the surfaces of a container. In accordance with another embodiment of the invention, the volume elements or "voxels" on the surface of the container being inspected which give rise to a side scatter signal are located. The measured side scatter signal coming from each of these voxels is compared to the signal that would be expected from a similar voxel located on the same surface of a similar container known to contain no sheet explosive. Voxels that have a significantly larger scatter signal than the expected value are marked as having excess scatter. Regions of the suitcase or container surface that have a high density of voxels with excess scatter are considered to potentially conceal sheet explosive. If the total area of the suspect region is above a certain minimum threshold, an alarm signal is initiated. In addition, the location and size of the suspect area can be displayed, or superimposed on a transmission image of the container.

A further alternate embodiment of the invention is particularly useful for determining whether explosive material has been concealed within an electronic device, such as a personal computer, stereo cassette recorder, or video camera. First, the location, dimensions and volume of all the objects in the container being inspected are determined from the side scatter distribution, as described above. For each object, the side scatter signal from all the volume elements within the object is summed, and the total divided by the measured volume of the object. This gives a measured value of the scatter per unit volume, $S_v$, for each reconstructed object in the container being inspected. Since the location of the object in the container is known, $S_v$ can be corrected for attenuation in the scatter signal due to overlying material between the object and the side scatter detector array.

Objects, if any, that are electronic devices may then be identified. This may be done with the assistance of an operator looking at a standard x-ray transmission image of the container. Alternatively, the system may identify electronic devices using "texture filters" applied to the transmission image in the following manner. Since electronic devices contain many small metallic electronic components, such as wires and transistors, an algorithm may easily identify an electronic device from its x-ray transmission image. The root-mean-square spread in the transmission intensity, for example, will be large for electronic devices compared with more homogenous objects. OOnce an object has been identified as an electronic device, the measured value of $S_v$ for the object is compared with the expected value for a similar electronic device that contains no explosive. If the measured value of $S_v$ is substantially larger than the expected value, it is a good indication that organic material has been concealed within the device, and an alarm signal may be generated.

In accordance with a further embodiment of the invention, beams of two or more energy compositions may be used to obtain further information with respect to the contents of a concealing enclosure. The energy content may be varied in temporal sequence, or, alternatively, multiple sources may illuminate different portions of the container simultaneously with different energy distributions. One of the most useful parameters for differentiating an explosive material with respect to other, benign, organic materials, is the density of the material, that is, the mass per unit volume $\rho$. The density of the material is typically measured in grams per cubic centimeter. The present invention may measure the density of concealed objects, as described above, by combining a measurement of the dimension of the object along the x-ray beam with a measure of the beam attenuation in the object. While dual-energy systems are known in a two dimensional context, such dual-energy imaging systems are incapable of directly measuring the density $\rho$.

A second parameter, the effective atomic number, or effective Z of the object, can also be used to discriminate between explosives and benign materials. However, the false alarm rate, when using effective Z only, tends to be considerably higher than when discriminating with density. This is because many benign objects have an effective Z similar to that of explosives. For example, the explosive PETN has an effective Z similar to many types of wood. The effective Z, however, can be combined with density in order to further reduce the false alarm rate for some types of explosives. Some benign materials such as sun screen lotions, for example, have a density in the range 1.1–1.4 g/cm$^3$, which is similar to many explosives. The effective Z for these materials, however, is markedly different from the explosives in the same density range. By combining density and effective Z into a two-parameter space, the true alarm rate is increased, while reducing the false alarm rate. The x-ray flux transmitted through a piece of material of thickness dx may be expressed, in analogy with equation 1, as:

$$N = N_0 e^{-\mu dx}, \quad (10)$$

where $N_0$ is the incident flux (in units of photons per area), and $\mu$ is the linear attenuation coefficient of an x-ray in the material. The ratio of the logarithm of the transmitted flux at two energies $E_1$ and $E_2$ is given by:

$$R = \frac{\log(N_1)}{\log(N_2)} = \frac{\mu_1}{\mu_2}, \quad (11)$$

where it has been assumed that the incident flux is the same in both cases. It can be seen that the ratio R is independent of the thickness dx of the material, and depends only on the linear attenuation coefficients $\mu_1$ and $\mu_2$ for the material at the two energies. These in turn, depend on the mean atomic number Z of the material, with this dependence strongest at lower x-ray energies. The ratio R can therefore be used to measure the effective atomic number Z of the material. As an example, the ratio R is 4.4 for iron ($Z_{eff}$=26) with 70 and 140 keV polychromatic x-ray beams. For wood ($Z_{eff}$=7.9) and polyethylene plastic ($Z_{eff}$=6.0), the ratio is 1.2 and 0.7, respectively. There is, therefore, a one-to-one mapping from the measured value of the ratio R to the effective Z of the material. For each concealed object, an apparatus in accordance with the invention may measure both the density $\rho$ and the effective atomic number Z. The former may be obtained by combining the side scatter and the transmission information as described above, and the latter is obtained by measuring the ratio R. The two parameters, density and effective Z, may provide an enhanced basis for threat identification. Dual energy x-ray beams may be obtained, for example, by switching the voltage supplied to the X-ray tube between every pair of scan lines This means that the container may be scanned by alternating low and high voltage x-ray beams. It should be noted that the described embodiments of the invention may be used in combination of two or more of the above embodiments in order to inspect the contents of the container. The described embodiments of the invention are intended to be merely exemplary and numerous variations and modifications will be apparent to those skilled in the art. All such variations and modifications are intended to be within the scope of the present invention as defined in the appended claims.

We claim:

1. A tomography system for analyzing a material concealed within an enveloping surface, the system comprising:
   a. a first source of penetrating radiation for emitting a beam along a beam axis disposed with an orientation with respect to the material and a second beam of penetrating radiation counterpropagating to the first beam;
   b. at least one array of segmented detectors disposed along a detector axis substantially parallel to the beam axis for detecting scattered radiation and producing signals corresponding at least to the scattered radiation; and
   c. a scanner arrangement for varying the orientation of the beam axis with respect to the material.

2. The tomography system in accordance with claim 1, wherein the counterpropagating beams are alternatingly illuminated.

3. The tomography system in accordance with claim 1, further comprising a plurality of collimators disposed in directions perpendicular to the beam axis for limiting the field of view of each segmented detector.

4. A method for analyzing material concealed within an enveloping surface, the method comprising:
   a. illuminating the enveloping surface with penetrating radiation;
   b. measuring a flux of penetrating radiation side-scattered into a detector by a plurality of voxels of the concealed material; and
   c. creating a three-dimensional map of the flux of penetrating radiation scattered by the plurality of voxels of the concealed material.

5. The method according to claim 4, further including:
   d. correcting the map of the flux of scattered penetrating radiation for attenuation in material disposed between the concealed material and the detector.

6. The method according to claim 4, further including:
   d. correcting the map of the flux of scattered penetrating radiation for a geometrical disposition of the concealed material with respect to the detector.

7. The method according to claim 4, further including:
   d. determining a dimension of the concealed material on the basis of a dimension of a region of enhanced scatter.

8. The method according to claim 4, further including:
   d. measuring an attenuation of penetrating radiation by the concealed material on the basis of penetrating radiation transmitted through the enveloping surface.

9. The method according to claim 8, further including:
   e. determining a dimension of the concealed material on the basis of a dimension of a region of enhanced scatter.
10. The method according to claim 9, further including:
   f. determining a density of the concealed material based on the attenuation of penetrating radiation by the concealed material and the dimension of the concealed material.
11. A method for analyzing material having edges, the material concealed within an enveloping surface, the method comprising:
   a. illuminating the enveloping surface with penetrating radiation propagating substantially along a beam axis;
   b. measuring a profile of penetrating radiation side-scattered by the concealed material to a single side of the concealed material; and
   c. locating the edges of the material on the basis of the profile of penetrating radiation side-scattered by the concealed material to the single side of the concealed material.
12. The method according to claim 11, further comprising the step of determining the dimensions of the concealed material along the beam axis.
13. The method according to claim 11, further including measuring penetrating radiation transmitted through the material.
14. The method according to claim 13, further including calculating an attenuation of penetrating radiation attributable to the material.
15. The method according to claim 13, further including deriving an attenuation per unit length characteristic of the material.
16. The method according to claim 11, further comprising the step of calculating the density of the concealed material on the basis of the attenuation and dimensions of the material.
17. The method according to claim 11, further comprising the step of raster-scanning the beam axis in a plane transverse to the beam axis.
18. The method according to claim 11, further including determining the three-dimensional shape of the concealed material on the basis of edges with respect to a plurality of beam positions.
19. The method according to claim 11, further comprising the step of imaging the concealed material.
20. The method according to claim 15, further comprising:
   a. comparing the attenuation of penetrating radiation per unit length in the concealed material with tabulated values; and
   b. determining the composition of the concealed material.
21. The method according to claim 20, further comprising:
   a. comparing the density of the concealed material with tabulated values; and
   b. determining the composition of the concealed material.
22. The method according to claim 14, further comprising the step of locating the material in the attenuation-thickness plane for determining a composition of the concealed material.

23. The method for analyzing concealed material within an enveloping surface, as set forth in claim 10, further comprising the step of categorizing a degree of threat constituted by said material.
24. The method for analyzing concealed material within an enveloping surface, as set forth in claim 11, further comprising the step of conveying the enveloping surface in a direction perpendicular to the beam axis.
25. The method according to claim 11, wherein the step of determining the edges of the concealed material includes the step of detecting a peak in the side-scattered radiation.
26. The method according to claim 11, wherein the step of illuminating the enveloping surface with penetrating radiation propagating substantially along an axis includes the step of alternating between illumination by two counterpropagating beams.
27. The method according to claim 17, further comprising deriving an attenuation of scattered radiation in a direction transverse to the beam axis.
28. The method according to claim 27, further comprising:
   a. measuring an attenuation of the illuminating penetrating radiation; and
   b. deriving an atomic number of the concealed material on the basis of at least the ratio of the attenuation of the illuminating penetrating radiation to the attenuation of the scattered radiation.
29. The method according to claim 17, further comprising correcting a calculated scatter per unit volume for matter intervening between the concealed material and the detector array.
30. The method according to claim 29, further comprising
   a. calculating a spread in attenuation of illuminating penetrating radiation across a specified volume of the enveloping surface;
   b. identifying types of objects concealed within the enveloping surface on the basis of the spread in measured attenuation over a specified volume of the enveloping surface.
31. The method according to claim 30, further comprising the step of comparing calculated scatter per unit volume against an expected scatter per unit volume based on the identified type of object concealed within the enveloping surface.
32. The method according to claim 11, wherein the step of illuminating the enveloping surface with penetrating radiation includes illuminating the enveloping surface alternatingly with differing energy distributions and determining an effective atomic number corresponding to the concealed material on the basis of the ratio of penetrating radiation transmitted through the material at a first and a second energy distribution.
33. The method according to claim 11, wherein the step of locating the edges of the material includes detecting discontinuities in the profile of side-scattered penetrating radiation.

* * * * *